United States Patent [19]

Ooms et al.

[11] Patent Number: 5,602,271
[45] Date of Patent: Feb. 11, 1997

[54] PROCESS FOR THE PREPARATION OF ARYL CARBONATES

[75] Inventors: Pieter Ooms; Hans-Josef Buysch, both of Krefeld; Norbert Schön, Darmstadt, all of Germany

[73] Assignee: Bayer Aktiengesellschaft, Leverkusen, Germany

[21] Appl. No.: 494,111

[22] Filed: Jun. 23, 1995

[30] Foreign Application Priority Data

Jul. 7, 1994 [DE] Germany ............... 44 23 863.0

[51] Int. Cl.⁶ ................ C07C 68/02; C07C 69/96
[52] U.S. Cl. .................................................. 558/274
[58] Field of Search ................................. 558/274

[56] References Cited

U.S. PATENT DOCUMENTS

| | | |
|---|---|---|
| 2,362,865 | 11/1944 | Tryon et al. . |
| 2,837,555 | 6/1958 | Lee . |
| 3,234,263 | 2/1966 | Kurkley et al. . |
| 5,239,105 | 8/1993 | Pews et al. ............... 558/274 |
| 5,288,474 | 2/1994 | Reichert et al. . |

FOREIGN PATENT DOCUMENTS

| | | |
|---|---|---|
| 0516355 | 12/1992 | European Pat. Off. . |
| 0547791 | 6/1993 | European Pat. Off. . |
| 0575745 | 12/1993 | European Pat. Off. . |
| WO91/06526 | 5/1991 | WIPO . |

*Primary Examiner*—Johann Richter
*Assistant Examiner*—Michael G. Ambrose
*Attorney, Agent, or Firm*—Connolly and Hutz

[57] ABSTRACT

Carbonates with aromatic ester groups are prepared by reaction of aromatic monohydroxy compounds with phosgene or with chloroformic acid esters of aromatic monohydroxy compounds, whereby operations are carried out at a temperature in the range of 50° to 450° C. and at a pressure in the range of 0.05 to 20 bar in the presence of metallates of the elements of groups IIIa, IVa, Va, VIa, IIIb, IVb, Vb, VIb, VIIb, and VIII of the Mendeleev periodic system as heterogeneous catalysts.

16 Claims, No Drawings

PROCESS FOR THE PREPARATION OF ARYL CARBONATES

The invention relates to a process for the preparation of carbonates with aromatic ester groups by reaction of aromatic monohydroxy compounds with phosgene or chloroformic acid esters of aromatic monohydroxy compounds, with elimination of hydrogen chloride, in the presence of metallates of the elements of groups IIIa, IVa, Va, VIa, IIIb, IVb, Vb, VIb, VIIb, and VIII of the Mendeleev periodic system as heterogeneous catalysts.

Carbonates with aromatic ester groups are suitable for the preparation of polycarbonates according to the melt transesterification process, for the preparation of phenyl urethanes, or are intermediates for active substances from the pharmaceutical and plant protection sector.

It is known that aryl carbonates may be obtained by phase interface phosgenation (Schotten-Baumann reaction) of aromatic hydroxy compounds. The use of solvents and sodium hydroxide solution is a disadvantage in this process, since a partial saponification of phosgene or chloroformic acid ester may take place in some cases due to the aqueous alkaline solution. In each case, large quantities of sodium chloride are obtained as a by-product. Moreover, care is required for solvent recovery.

Condensation without the use of solvents in the presence of tetramethylammonium halides as catalysts has, therefore, been proposed (U.S. Pat. No. 2,837,555). The quantities of catalyst required are, however, relatively large. As a rule, it is necessary to operate with 5 to 7% by wt. of catalyst, based on the quantity of phenol used, in order to obtain economic rates of reaction; the reaction temperatures of 180° C. to 215° C. involve the risk of decomposition of the thermolabile tetramethylammonium halides. Moreover, the catalyst has to be removed subsequently by washing with water, as a result of which its recovery is made much more difficult. Moreover, far more than the stoichiometrically required quantity of phosgene is consumed.

According to a further process (U.S. Pat. No. 3,234,263), diaryl carbonates are obtained by heating phenyl chloroformates in the presence of large quantities of alkali (alkaline earth) compounds with tertiary nitrogen bases as catalysts. Said process has the disadvantage, however, that high temperatures have to be used and the catalysts such as alkali (alkaline earth) compounds must be partially dissolved in order to achieve reaction times that are economically acceptable. In this process, half of the phosgene originally used is lost in the form of $CO_2$. In addition, the chloroformic acid esters must be synthesised in a prior separate process stage.

According to U.S. Pat. No. 2,362,865, diaryl carbonates are obtained by phosgenation of aromatic hydroxy compounds in the presence of metallic titanium, iron, zinc, and tin or in the form of soluble salts thereof, particularly the chlorides and phenolates. Although very good yields are obtained, it is difficult to separate the catalysts from the products. In distillation operations, even a certain volatility of said compounds as well as thermal decompositions due to said compounds, must be taken into account leading to impurities, quality reductions, and losses of yield.

It seems appropriate, therefore, to use heterogeneous, insoluble catalysts which facilitate substantially the work-up of the reaction mixture. Proposals have also been made to this end. For example, according to the teaching of EP-A-516 355, particularly aluminium trifluoride is recommended, which is applied optionally to supports such as aluminosilicates. The synthesis of aluminium fluoride is, however, very complicated and more expensive due to the handling of fluorine or hydrofluoric acid. Moreover, metal salts on porous supports are described in WO 91/06526 as catalysts for the reactions according to the invention. As emerges from the test examples, fully continuous phosgenation of phenol on such catalysts is possible only in the gas phase, which entails, however, relatively high reaction temperatures and the risk of decomposition of the sensitive chloroformic acid esters. Evidently, phosgenation of phenol with said catalysts is not feasible in the liquid phase, since the hot liquid phenol washes out the active catalyst constituents.

The object of the invention was, therefore, to develop more readily accessible, effective, heterogeneous catalysts.

It has now been found that metallates of elements of groups IIIa, IVa, Va, VIa, IIIb, IVb, Vb, VIb, VIIb, and VIII of the Mendeleev periodic system, such as, for example, titanates, represent excellent catalysts for the reaction of phosgene or chloroformic acid esters with aromatic hydroxy compounds. This is particularly surprising and unexpected because, according to the prior teaching of WO 91/06526, oxides of metals such as titanium and zirconium are mentioned in preference as resistant and inert support materials.

The object of the present invention is, consequently, a process for the preparation of aryl carbonates by reaction of aromatic monohydroxy compounds with phosgene or chloroformic acid esters of aromatic monohydroxy compounds, which is characterised in that operations are carried out at temperatures in the region of 50° to 450° C., optionally at a pressure of 0.05 to 20 bar in the presence of metallates of elements of groups IIIa, IVa, Va, VIa, IIIb, IVb, Vb, VIb, VIIb, and VIII of the Mendeleev periodic system as heterogeneous catalysts.

The process according to the invention has the great advantage that the catalyst may be separated very easily and no impurities remain in the crude reaction product. As a result, work-up is simplified considerably.

Aromatic monohydroxy compounds for the process according to the invention are those having the formula $$Ar^1\text{---}OH \qquad (I),$$

wherein $Ar^1$ means phenyl, naphthyl, anthryl, phenanthryl, indanyl, tetrahydronaphthyl or the radical of a 5- or 6-membered aromatic heterocycle with 1 or 2 heteroatoms from the group of N, O and S, whereby said isocyclic and heterocyclic radicals may be substituted by 1 or 2 substituents such as straight-chain or branched $C_1$–$C_4$ alkyl, straight-chain or branched $C_1$–$C_4$ alkoxy, which may be substituted with phenyl, cyano and halogen (e.g. F, Cl, Br), and whereby, moreover, the heterocyclic radicals may be linked with a fused benzene nucleus.

Examples of aromatic monohydroxy compounds having the formula (I) are: phenol, o-, m- and p-cresol, o-, m- and p-isopropylphenol, the corresponding halogen and alkoxy phenols such as p-chlorophenol and p-methoxyphenol, also monohydroxy compounds of naphthaline, anthracene and phenanthrene, also 4-hydroxypyridine and hydroxyquinoline. Optionally substituted phenols are used in preference, phenol itself in quite particular preference.

The process according to the invention may be carried out both with phosgene and with chloroformic acid esters of aromatic monohydroxy compounds. If it is carried out with phosgene, the chloroformic acid ester is produced initially, which is converted to the diaryl carbonate with additional aromatic monohydroxy compound present in the reaction mixture.

Starting from chloroformic acid esters and an aromatic monohydroxy compound, symmetrical or asymmetrical carbonates may be obtained.

Suitable aromatic chloroformic acid esters for the process according to the invention are those having the formula (II)

$$Ar^1—OCOCl \quad (II),$$

wherein $Ar^1$ has the meaning given in formula (I).

Suitable metallates within the meaning of the invention are compounds having the general formula (III)

$$A_xB_yO_z \quad (III),$$

in which

A stands for a mono-, di- and/or trivalent metal cation, and

B stands for a tri-, tetra-, penta- and/or hexavalent metal cation, and x stands for a number from 1 to 4, and y stands for a number of 1 or 2, and z stands for number of 3, 6, 7, or 9.

Examples of metal cation A that may be mentioned are:

monovalent metal cations such as Li, Na, K, Rb, Cs, Cu, Ag, and Tl, divalent metal cations such as Be, Mg, Ca, Sr, Ba, Zn, Hg, Sn, Pb, Fe, Mn, Co, Ni, trivalent metal cations such as B, Al, Ga, Y, Tl, Bi, Fe, Mn, Co, Cr, V, Mo, Na, K, Be, Mg, Ca, Ba, Fe, Ni, Zn, Al, Pb, Cr, V, and Mo are preferred, Na, K, Mg, Ca, Ba, Fe, Pb, Ni, and Zn are particularly preferred.

Examples of metal cation B that may be mentioned are:

trivalent metal cations such as Sc, Y, Cr, Mn, Fe, and Ga, tetravalent metal cations such as Ti, Zr, Hf, V, Nb, Mo, Ru, Os, Re, Ir, Sn, and Pb, pentavalent metal cations such as V, Nb, Ta, Re, Ru, Os, Rh, Ir, Sb, and Bi, hexavalent metal cations such as Mo, W, and Te, Ti, Zr, Nb, Ta, V, Mo, W and Sn are preferred, Ti, Zr, Nb, and Ta are particularly preferred.

One or more metal cations A or metal cations B may also occur together in a different valency in the metallates. Metallates particularly suitable as heterogeneous catalysts are metallates with a perovskite and pyrochlore structure.

They may be present in crystalline form in various modifications. They may be wholly or partially amorphous.

Such metallates and their origin or the production process for such compounds are described, for example, in Kirk-Othmer, Encyclopedia of Chemical Technology, 3rd edition, volume 20, page 410 ff, volume 22, page 656, volume 23, page 153 ff, volume 19, page 651 ff, volume 13, page 768, 782 ff, New York 1969/1983, Ullmann's Encyclopedia of Industrial Chemistry, 5th edition, volume 17 ff, page 431, Weinheim 1966, and EP 0 547 791, 0 575 745.

Both metallates from natural sources, i.e. various minerals such as, e.g. ilmenite or perovskite, but also a synthetic metallates such as those from precursors, for example, metal salts, metal oxides, and metal alkoxides are suitable.

The metallates to be used in the process according to the invention are preferably titanates, zirconates, niobates and tantalates, for example lithium titanate, sodium titanate, potassium titanate, barium titanate, strontium titanate, calcium titanate (occurring as perovskite in monoclinic, pseudocubic form), magnesium titanate (occurring in rhombohedral form), aluminium titanate (occurring as tielite in both the α and β modification), cadmium titanate (occurring in orthorhombic and cubic structure), cobalt titanate (occurring in rhombohedral and cubic form), iron titanate (occurring as ilmenite or pseudobrookite), manganese titanate (occurring in hexagonal and cubic form), nickel titanate, zinc titanate (spinel form), lead titanate (rhombic pyramides), lithium zirconate, sodium zirconate, potassium zirconate, barium zirconate, calcium zirconate, strontium zirconate, iron zirconate, lanthanum zirconate, yttrium zirconate, sodium niobate, potassium niobate, calcium niobate, magnesium niobate, zinc niobate, iron niobate (occurring as columbite), nickel niobate, lead niobate, sodium tantalate, potassium tantalate, lead tantalate, magnesium stannate, calcium tungstate, barium tungstate, zinc molybdate, lead molybdate, and mixed metallates such as lead magnesium niobate, iron manganese niobate, lead magnesium tantalate, and barium zinc tantalate.

The metallates within the meaning of the invention may be used in the dried, partially dried form or as hydrates.

As a result of successive dehydration (calcining) of mixed metal hydroxides and metal oxides/hydroxides at temperatures of 80° to above 1200° C., partially dehydrated metallates are produced initially, which still contain appreciable quantities of hydroxyl groups and change over into the anhydrous metallates as dehydration proceeds. Depending on the nature of the starting hydroxide, or oxide/hydroxide, various modifications of the metallates mentioned above may be passed through during calcining.

Preferred metallates have BET surfaces of 0.1 to 500 m$^2$/g, in particular preference those of 0.5 to 450 m$^2$/g and in quite particular preference those of 1 to 400 m$^2$/g. Acid, neutral and basic metallates may be used.

The catalysts may be used, e.g. as powder or moulded bodies and separated after the reaction, e.g. by filtration, sedimentation or centrifuging. If arranged as a fixed bed, the metallates are used preferably as moulded bodies, e.g. as spheres, cylinders, rods, hollow cylinders, rings etc.

During operation with suspended catalyst in stirred vessels or bubble columns, the metallate catalysts are used in quantities of 0.5 to 100% by wt., preferably 5 to 100% by wt., and in particular preference 5 to 50% by wt., based on the quantity of monohydroxy compound used.

In the event of continuous operation in counter-current or co-current or in the trickle phase or in the gas phase on the fixed bed catalyst, catalyst loadings of 0.1 to 20 g of aromatic hydroxy compound per g of catalyst per hour are used, preferably 0.2 to 10 g.g$^{-1}$.h$^{-1}$ and in particular preference 0.2 to 5 g.g$^{-1}$.h$^{-1}$. The metallates used in batchwise tests may be used repeatedly without purification, with the same starting materials. If the starting materials are changed, the metallates are purified expediently by extraction with inert solvents, such as those mentioned by way of example further below as reaction media, or with alcohols such as methanol, ethanol, isopropanol or butanol, with esters or amides of acetic acid, or by treatment with super-heated steam or air.

During continuous operation, the metallates used may remain in the reactor for a long period. Regeneration may take place optionally by passing over super-heated steam, optionally with the addition of minor quantities of air (about 0.1 to 20% by wt., based on the quantity of steam used) at 150° to 800° C., or by passing over 0.01 to 20% by wt., of oxygen-containing dilution gases such as nitrogen or carbon dioxide or by means of carbon dioxide alone at 200° to 800° C. The preferred regeneration temperature is 150° to 700° C., in particular preference 200° to 600° C.

The process according to the invention is carried out at a temperature in the region of 50° to 450° C., preferably 100° to 400° C., in particular preference at 100° to 350° C. Whilst the process of the invention is being carried out, the temperature may be altered in the named range, preferably increased.

The process according to the invention is carried out at a pressure of 0.05 to 20 bar, preferably 1 to 5 bar.

It is possible to carry out the process according to the invention with the assistance of solvents such as aliphatic and aromatic hydrocarbons such as pentane, hexane, octane, benzene, xylene isomers, diethyl benzene, alkylnaphthalenes, biphenyl; halogenated hydrocarbons such as dichloromethane, trichloroethylene etc. The process according to the invention may be carried out both in the gas phase and in the liquid phase.

In preference, the process is carried out in the melt, for example, by introducing phosgene or a choroformic acid ester having the formula (II) into a suspension of a metallate in a melt of the aromatic monohydroxy compound having the formula (I), and separating the catalyst e.g. by filtration or centrifuging after completion of the reaction.

The process is carried out in the gas phase by evaporating phosgene and phenol and passing the mixture over a bed of a catalyst in lump form arranged in a tube.

Another preferred embodiment of the synthesis is that of gassing a melt of the aromatic monohydroxy compound having the formula (I), with metallate catalyst suspended therein, with phosgene or phosgene-hydrogen chloride mixtures or with chloroformic acid esters having the formula (II) in a continuously operating bubble column or bubble column cascade.

Another preferred embodiment is the co-current process in which aromatic hydroxy compounds having the formula (I) and phosgene or chloroformic acid esters having the formula (II) are introduced in co-current, for example, from above onto a catalyst bed arranged in a tube, and hydrogen chloride and phosgenation products are drawn off at the bottom of the tube.

Another preferred embodiment with particularly favourable results is that of carrying out the reaction according to the invention in counter-current in the trickle phase, wherein the aromatic monohydroxy compound having the formula (I) is introduced from above as a melt or in the form of a solution on to a bed of metallate, and a stream of phosgene or chloroformic acid ester is passed from below in counter-current to said liquid stream. Advantageously, said embodiment is carried out in a vertical tubular reactor which may also contain intermediate plates for improving the distribution of gas and liquid stream. Another preferred embodiment is the gas phase process at temperatures of 150° to 450° C., preferably 200° to 350° C. with pressures of 0.05 to 20, preferably 0.1 to 4 bar, in particular preference 0.1 to 3 bar.

In said process, the pressure is varied with the temperature such that the components remain in the gas phase and do not condense on the catalyst fill.

The molar ratio of the reactants aromatic monohydroxy compounds having the formula (I) to phosgene is 0.5 to 8:1, preferably 1.5 to 3:1. The equivalent molar ratio in this case is 2:1.

The aromatic monohydroxy compound is reacted in a corresponding manner with a chloroformic acid ester in a molar ratio of 0.25 to 4:1, preferably 0.8 to 1.5:1. In this case, the molar ratio is 1:1.

The crude aromatic carbonate obtained by heterogeneous catalysis is often already very pure and may be used in this form for many purposes after degassing residual hydrogen chloride or other volatile substances. For more demanding applications, the carbonate may be purified further if necessary, e.g. by distillation or crystallisation.

EXAMPLES

Example 1

In a flat flange vessel with flow breakers, a gas dispersion stirrer and reflux condenser, 141 g (1.50 mole) of phenol were treated continuously at 140° C. with 0.75 mole/h of phosgene gas in the presence of 14.1 g (10% by wt. based on phenol) of a magnesium titanate in powder form made by Bayer. After a reaction time of about 2 h, the phenol conversion was 36.4%, only (58.3 g) diphenyl carbonate being formed. The selectivity was >99%.

Example 2

Example 1 was repeated at 140° C. with 14.1 g of a barium titanate in powder form made by Aldrich. After a reaction time of 2 h, the phenol conversion was 31.6%, only (50.1 g) diphenyl carbonate being formed. The selectivity was about 99%.

Example 3

Example 1 was repeated at 140° C. with 14.1 g of a lead titanate in powder form made by Aldrich. After a reaction time of 2 h, the phenol conversion was 39.3%, only (62.8 g) diphenyl carbonate being formed. The selectivity was greater than 99%.

Example 4

Example 1 was repeated at 140° C. with 14.1 g of a sodium titanate in powder form made by Bayer. After a reaction time of 2 h, the phenol conversion was 21.5%, only (34.1 g) diphenyl carbonate being formed. The selectivity was about 99%.

Example 5

Example 1 was repeated at 140° C. with 14.1 g of a calcium titanate in powder form made by Aldrich. After a reaction time of 2 h, the phenol conversion was 35.4%, 51.6 g of diphenyl carbonate being formed. The selectivity was about 91%.

Example 6

Example 1 was repeated at 140° C. with 14.1 g of a magnesium niobate in powder form made by Starck. After a reaction time of 2 h, the phenol conversion was 16.0%, 2.1 g of phenyl chloroformate and 24.1 g of diphenyl carbonate being formed. The selectivity to carbonates was >99%.

Example 7

Example 1 was repeated at 140° C. with 14.1 g of a zinc niobate in powder form made by Starck. After a reaction time of 2 h, the phenol conversion was 6.3%, 1.1 g of phenyl chloroformate and 9.2 g of diphenyl carbonate being formed. The selectivity to carbonates was approx. 98%.

Example 8

Example 1 was repeated at 140° C. with 14.1 g of an iron niobate in powder form made by Starck. After a reaction time of 2 h, the phenol conversion was 4.1%, 2.3 g of phenyl chloroformate and 4.2 g of diphenyl carbonate being formed. The selectivity to carbonates was approx. 90%.

Example 9

Example 1 was repeated at 140° C. with 14.1 g of a barium zinc tantalate in powder form made by Starck. After a reaction time of 2 h, the phenol conversion was 8.4%, 3.4 g of phenyl chloroformate and 10.8 g of diphenyl carbonate being formed. The selectivity to carbonates was approx. 97%.

Example 10 (for comparison)

Example 1 was repeated at 140° C. without the addition of metallate. After a reaction time of 2 h, the phenol conversion was less than 0.2%.

Example 11

In a three-necked flask with thermometer and reflux condenser, a mixture of 9.4 g (0.10 mole) of phenol and 15.7 g (0.10 mole) of phenyl chloroformate is heated to 100° C. in the presence of 0.94 g (10% by wt. based on phenol) of a magnesium titanate in powder form made by Bayer. After a reaction time of 5 h, a phenol conversion of 78.1% to diphenyl carbonate is found. The carbonate selectivity was >99%.

Example 12

Example 11 was repeated at 120° C. with the same catalyst. After a reaction time of 2 h, the phenol conversion to diphenyl carbonate was 88.3%. The carbonate selectivity was >99%.

Example 13

Example 11 was repeated at 140° C. with the same catalyst. After a reaction time of 0.5 h, the phenol conversion to diphenyl carbonate was 45.5%. The carbonate selectivity was >99%.

Example 14

Example 11 was repeated at 160° C. with the same catalyst. After a reaction time of 1 h, the phenol conversion to diphenyl carbonate was 97.8%. The carbonate selectivity was >99%.

Example 15

Example 11 was repeated at 160° C. with 0.94 g of barium titanate in powder form made by Aldrich. After a reaction time of 0.5 h, the phenol conversion to diphenyl carbonate was 88.2%. The carbonate selectivity was >99%.

Example 16

Example 11 was repeated at 160° C. with 0.94 g of lead titanate from Aldrich. After a reaction time of 0.5 h, the phenol conversion to diphenyl carbonate was 99.2%. The carbonate selectivity was >99%.

Example 17

Example 11 was repeated at 160° C. with 0.94 g of a sodium titanate in powder form made by Bayer. After a reaction time of 0.5 h, the phenol conversion to diphenyl carbonate was 82.2%. The carbonate selectivity was >99%.

Example 18

Example 11 was repeated at 140° C. with 0.94 g of calcium titanate in powder form made by Aldrich. After a reaction time of 0.5 h, the phenol conversion to diphenyl carbonate was 89.1%. The carbonate selectivity was >99%.

Example 19

Example 11 was repeated at 160° C. with 0.94 g of a magnesium niobate in powder form made by Starck. After a reaction time of 3 h, the phenol conversion to diphenyl carbonate was 64.7%. The carbonate selectivity was >99%.

Example 20

Example 11 was repeated at 160° C. with 0.94 g of zinc niobate in powder form made by Starck. After a reaction time of 6 h, the phenol conversion to diphenyl carbonate was 28.6%. The carbonate selectivity was >99%.

Example 21

Example 11 was repeated at 160° C. with 0.94 g of iron niobate made by Starck. After a reaction time of 5 h, the phenol conversion to diphenyl carbonate was 65.5%. The carbonate selectivity was approx. 97%.

Example 22

Example 11 was repeated at 160° C. with 0.94 g of nickel niobate in powder form made by Starck. After a reaction time of 6 h, the phenol conversion to diphenyl carbonate was 16.8%. The carbonate selectivity was >99%.

Example 23

Example 11 was repeated at 160° C. with 0.94 g of a barium zinc tantalate in powder form made by Starck. After a reaction time of 4 h, the phenol conversion to diphenyl carbonate was 74.9%. The carbonate selectivity was approx. 98%.

We claim:

1. A process for the preparation of aryl carbonates by reaction of aromatic monohydroxy compounds with phosgene or chloroformic acid esters of aromatic hydroxy compounds, wherein the reaction is carried out at a temperature in the region of 50° to 450° C., at a pressure of 0.05 to 20 bar in the presence of one or more metallates of type $A_xB_yO_z$ as heterogeneous catalysts, wherein:

A represents a mono-, di-, or trivalent metal cation;

B represents a tri-, tetra-, penta- or hexavalent metal cation;

x represents a number in the range of 1 to 4;

y represents a number in the range of 1 to 2;

z represents a number taken from the group consisting of 3, 6, 7, and 9; provided that A and B do not represent the same metal cation.

2. The process of claim 1 carried out as a non-fully continuous or a fully continuous operation wherein the metallate catalysts have surfaces of 0.1 to 500 $m^2/g$, determined by the BET method, and are used in quantities of 0.5 to 100% by weight, based on the quantity of monohydroxy compound, in the case of a non-fully continuous operation, or with loadings of 0.1 to 20 g of monohydroxy compound per g of catalyst and per hour in the case of a fully continuous operation.

3. The process of claim 1, wherein metal cation A is a monovalent metal cation selected from the group consisting of Li, Na, K, Rb, Cs, Cu, Ag, and Tl, or a divalent metal cation selected from the group consisting of Be, Mg, Ca, Sr, Ba, Zn, Hg, Sn, Pb, Fe, Mn, Co, and Ni, or a trivalent metal cation selected from the group consisting of B, Al, Ga, Y, Tl, Bi, Fe, Mn, Co, Cr, V, and Mo, and the metal cation B is a trivalent metal cation selected from the group consisting of Sc, Y, Cr, Mn, Fe, and Ga, or a tetravalent metal cation selected from the group consisting of Ti, Zr, Hf, V, Nb, Mo, Ru, Os, Re, Ir, Sn, and Pb, or a pentavalent metal cation selected from the group consisting of V, Nb, Ta, Re, Ru, Os, Rh, Ir, Sb, and Bi, or a hexavalent metal cation selected from the group consisting of Mo, W, and Te.

4. The process of claim 1, wherein metal cation A is selected from the group consisting of Na, K, Mg, Ca, Ba, Fe, Pb, Ni and Zn, and wherein metal cation B is selected from the group consisting of Ti, Zr, Nb and Ta.

5. The process of claim 1, wherein the metallate comprises powdered magnesium titanate.

6. The process of claim 1, wherein the metallate comprises powdered barium titanate.

7. The process of claim 1, wherein the metallate comprises powdered lead titanate.

8. The process of claim 1, wherein the metallate comprises powdered sodium titanate.

9. The process of claim 1, wherein the metallate comprises powdered calcium titanate.

10. The process of claim 1, wherein the metallate comprises powdered magnesium niobate.

11. The process of claim 1, wherein the metallate comprises powdered zinc niobate.

12. The process of claim 1, wherein the metallate comprises powdered iron niobate.

13. The process of claim 1, wherein the metallate comprises powdered barium zinc tantalate.

14. The process of claim 1, wherein the metallate comprises powdered nickel niobate.

15. The process of claim 1, carried out at temperature of 100° to 350° C.

16. The process of claim 1, carried out at temperature of 120° to 160° C.

* * * * *